United States Patent [19]

Beech, Jr. et al.

[11] Patent Number: 5,059,738
[45] Date of Patent: Oct. 22, 1991

[54] METHOD FOR REACTIVATING MTG PROCESS CATALYST

[75] Inventors: James H. Beech, Jr., Wilmington, Del.; Francis P. Ragonese, Cherry Hill, N.J.

[73] Assignee: Mobil Oil Corporation, Fairfax, Va.

[21] Appl. No.: 489,991

[22] Filed: Mar. 7, 1990

[51] Int. Cl.$^5$ .......................... C07C 1/20; C07C 1/00; B01J 29/38; B01J 38/04
[52] U.S. Cl. ..................................... 585/469; 502/34; 502/56; 585/408; 585/639; 585/640; 585/733
[58] Field of Search .................... 502/34, 56; 585/469, 585/639, 640, 733, 408

[56] References Cited

U.S. PATENT DOCUMENTS

| 3,398,208 | 3/1965 | Ward | 260/674 |
| 4,417,088 | 11/1983 | Miller | 585/533 |
| 4,544,781 | 10/1985 | Chao et al. | 585/469 |

*Primary Examiner*—Paul E. Konopka
*Attorney, Agent, or Firm*—Alexander J. McKillop; Charles J. Speciale; L. G. Wise

[57] ABSTRACT

It is disclosed that in a fixed bed process for the conversion of $C_1$–$C_4$ oxygenates in contact with acidic, medium pore, shape selective metallosilicate catalyst particles to produce gasoline boiling range hydrocarbons, including the step of reactivating spent catalyst at elevated temperature, the cycle time between regenerations can be substantially improved by reactivating the spent catalyst at reduced pressure and elevated temperature in contact with a stream of inert purge gas. Preferably, the reactivation is carried out at a reduced pressure from sub-atmospheric to 1400 kPa using nitrogen as a purge gas. Other purge gases include light paraffinic hydrocarbons, refinery fuel gas and Group VIII gases of the Periodic Table of the Elements.

20 Claims, 5 Drawing Sheets

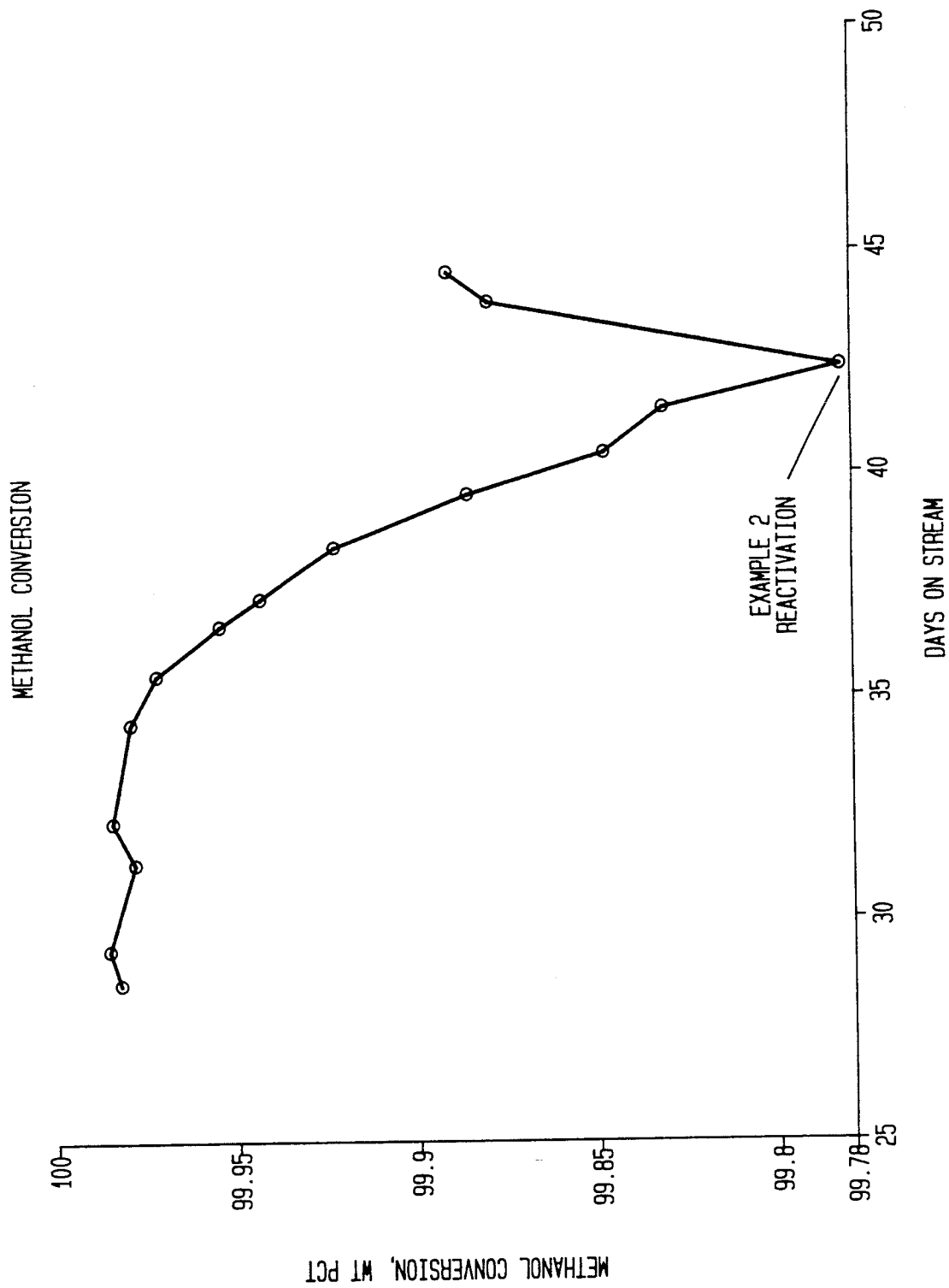

5,059,738

METHOD FOR REACTIVATING MTG PROCESS CATALYST

This invention relates to the process for the zeolite catalyzed conversion of oxygenated hydrocarbons to higher molecular weight products. The invention particularly relates to the ZSM-5 catalyzed fixed bed conversion of methanol or dimethylether to gasoline boiling range hydrocarbons. More particularly, the invention relates to an improved process for reactivating or regenerating spent zeolite catalyst in the methanol-to-gasoline (MTG) process.

BACKGROUND OF THE INVENTION

Processes for converting lower alcohols such as methanol to hydrocarbons are known and have become of great interest in recent times because they offer an attractive way of producing liquid hydrocarbon fuels, especially gasoline, from sources which are not of liquid petroliferous origin. In particular, they provide a way by which methanol can be converted to gasoline boiling range products in good yields. The methanol, in turn, may be readily obtained from coal by gasification to synthesis gas and conversion of the synthesis gas to methanol by well-established industrial processes. As an alternative, the methanol may be obtained from natural gas by other conventional processes.

The conversion of methanol to hydrocarbon products may take place in a fluidized bed process as described, for example, in U.S. Pat. Nos. 4,071,573 and 4,138,440, or in a fixed bed as described in U.S. Pat. Nos. 3,998,899, 3,931,349 and 4,035,430. In the fixed bed process, the methanol is usually first subjected to a dehydrating step, using a catalyst such as gamma-alumina, to form an equilibrium mixture of methanol, dimethyl ether (DME) and water. This mixture is then passed over a catalyst such as zeolite ZSM-5 which brings about the conversion to the hydrocarbon products which are mainly in the range of light gas to gasoline. The water may be removed from the methanol dehydration products prior to conversion to hydrocarbons as may the methanol which can be recycled to the dehydration step, as described in U.S. Pat. No. 4,035,430. Removal of the water is desirable because the catalyst may tend to become deactivated by the presence of the water vapor at the reaction temperatures employed, but this step is by no means essential.

The conversion of oxygenates, or more particularly methanol, to gasoline, typically referred to as the MTG process, is highly energy efficient. The hydrocarbons from the conversion contain 95 percent of the energy in the original methanol feed; the other five percent is released as exothermic heat and used during the conversion reaction. Recycling of process gas limits the temperature rise across the fixed catalyst bed to less than 95° C. Also during the reaction, a small amount of hydrocarbon is deposited on the catalyst as coke, requiring periodic catalyst regeneration. Operation of the process, however, is continuous because additional reactors, arranged in parallel, permit an individual reactor to swing from operation to regeneration while another goes from regeneration to operation. The final gasoline yield from the fixed bed process, after alkylating the light olefins formed, is about 85–90 percent by weight of the total hydrocarbons formed. The remaining hydrocarbons are available mostly as liquid petroleum gas (LPG) and a small amount of fuel gas.

The conversion of oxygenates is described in depth by C. D. Chang, Catal. Rev.-Sci. Eng., 25, 1 (1983) and in U.S. Pat. Nos. 3,931,349 to Kuo and 4,404,414 to Penick et al. These references are incorporated herein in their entirety.

Major problems facing research workers in the field of the MTG process include improvements in cycle average yield of gasoline and the extension of catalyst cycle life. Improvements in yield and catalyst life are known to be inextricably related, whereby advances in one problem area are typically achieved at the expense of the other. Process improvements leading to the common enhancement of gasoline yield and catalyst life have been most elusive. One factor that complicates the effort of research workers to achieve the desired advances in yield and catalyst cycle life is the requirement that the MTG process operate at or near quantitative methanol conversion. Less than quantitative conversions, or "methanol breakthrough," presents severe problems in waste disposal and/or methanol recovery which quickly leads to punishing economic penalties and, therefore, is to be avoided. Accordingly, whatever advances research workers are to make in yield and catalyst life for MTG improvements must be made while maintaining essentially quantitative conversion of methanol.

The MTG process is a gas phase process which produces isoparaffins and aromatics with virtually no oligomer formation. The coke formed in the process is harder and more condensed than that from other processes such as zeolite catalyzed olefin oligomerization. Accordingly, it is much harder to remove. It is, however, well known that deactivated or aged zeolite oxygenate conversion catalyst can be regenerated by contacting the catalyst at elevated temperature with an oxygen-containing gas such as air to effect controlled burning of coke from the deactivated catalyst. While such a conventional regeneration procedure can restore catalytic activity diminished by coke formation in the catalyst during the conversion reaction, regeneration in this manner can lead to catalyst damage requiring more frequent, and expensive, catalyst replacement. There is, therefore, a continuing need to find better methods to regenerate deactivated catalyst in fixed beds in order to lengthen time on stream, or cycle length.

Accordingly, it is an object of the present invention to provide a more effective and non-oxidizing process for the reactivation of a fixed bed containing spent or deactivated zeolite catalyst.

Another object of the invention is to provide a catalyst reactivation method which would extend the cycle time between regeneration of fixed bed zeolite catalyst compared to conventional reactivation methods.

Yet another object of the present invention is to provide a process more effective and useful for the reactivation of deactivated zeolite catalyst for lower oxygenate conversion processes.

SUMMARY OF THE INVENTION

The discovery has been made that in a fixed bed process for the conversion of $C_1$–$C_4$ oxygenates in contact with acidic, medium pore, shape selective metallosilicate catalyst particles to produce gasoline boiling range hydrocarbons, including the step of reactivating spent catalyst at super atmospheric pressure and elevated temperature, the cycle time between regenerations can be substantially improved by reactivating the spent catalyst at reduced pressure and elevated temperature in contact with a stream of inert purge gas. Preferably, the reactivation is carried out at a reduced pressure from sub-atmospheric to 1400 KPa using nitrogen as a purge gas. Other purge gases include light paraffinic hydrocarbons and Group VIII gases of the IUPAC Periodic Table of the Elements.

More particularly, the invention comprises a process for the conversion of lower aliphatic oxygenated hydrocarbon to gasoline or gasoline and distillate boiling range hydrocarbons. The novel process includes the steps of passing the feedstock through a reactor containing a fixed bed of acidic, shape selective, medium pore zeolite catalyst particles at conditions sufficient to effect said conversion; separating effluent from the reactor and recovering gasoline or gasoline and distillate boiling range hydrocarbons; interrupting the feedstock flow to the reactor coincident with catalyst deactivation and loss in feedstock conversion rate; and passing inert purge gas to the reactor at elevated temperature and reduced pressure whereby deactivated catalyst in the reactor is reactivated.

In the process of the present invention, spent or otherwise deactivated catalyst is reactivated at a temperature between 300° C. and 400° C. at about atmospheric pressure using nitrogen as purge gas. The preferred reactivation temperature is 360° C.

DESCRIPTION OF THE FIGURES

FIG. 5 is a plot of methanol conversion history for Example 2 of the invention.

DETAIL DESCRIPTION OF THE INVENTION

Figure 1:
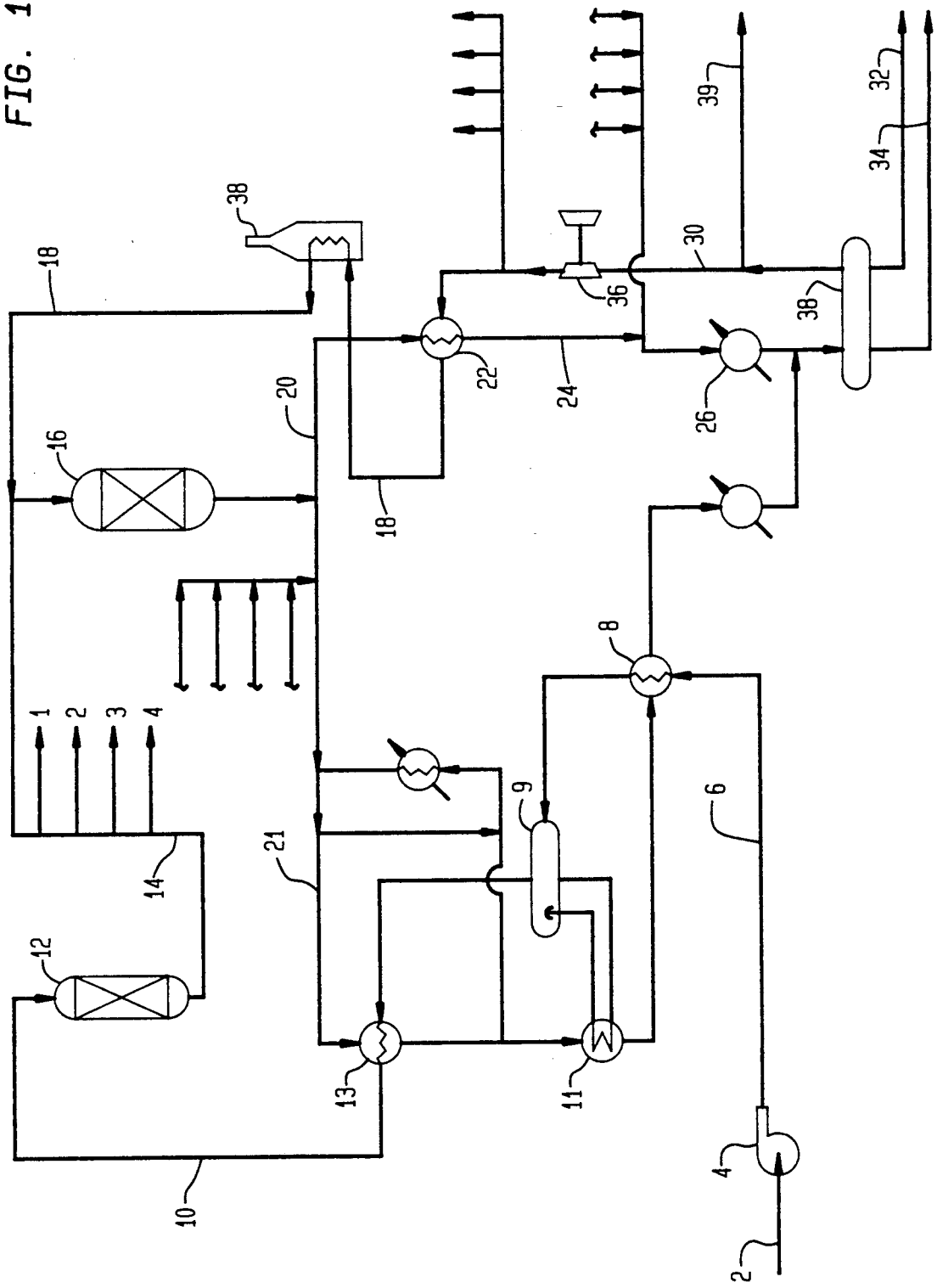
FIG. 1 is a process flow diagram of the MTG process.

The MTG process is useful for the conversion of a number of differing oxygenated organic compounds into hydrocarbon products. The process is useful for the conversion of aliphatic compounds including lower alcohols such as methanol, ethanol and propanol, ethers such as DME and diethyl ether, ketones such as acetone and methyl ethyl ketone, aldehydes such as acetaldehyde, esters such as methyl formate, methyl acetate and ethyl acetate, carboxylic acids such as acetic acid, butyric acid and their anhydrides e.g., acetic anhydride. Examples of conversions of such compounds may be found in U.S. Pat. Nos. 3,907,915, 3,894,107, 3,894,106, 3,894,103, 3,894,104, and 3,894,105 to which reference is made for details of the conversions. The product in each case will be a hydrocarbon mixture ranging from light gas to heavier fractions ($C_{10+}$) but will generally be concentrated in the gasoline boiling range ($C_5$-220° C.). The process is particularly useful in the catalytic conversion of methanol to hydrocarbons in the gasoline boiling range and, for convenience, the process will be described below with reference to such a process although it should be remembered that the principles are applicable to a broader range of conversion, as set out above.

If methanol is used as the starting material for the process it is preferred to subject it to an initial dehydration step to form an intermediate product comprising dimethyl ether (DME). The DME is then passed to the hydrocarbon step with either complete, partial or no separation of the unreacted methanol and the water produced as a by-product of the dehydration. However, it is not essential to carry out this dehydration even though it is preferred. It is possible to dehydrate only part of the methanol with, for example, the dehydration product going to one reactor and the raw methanol going to another.

Because the oxygenated charge may be fed into the reactors in different forms, e.g., methanol and DME, it will often be convenient, for purposes of calculating recycle ratio and other factors, to base the calculations upon a single equivalent charge. For example, if both methanol and DME are fed to the reactors, the total charge may be reduced to a basis of "methanol equivalents" in which one mole of DME is equal to two methanol equivalents. Thus, the reactant flow at any point may be readily reduced to a single value from which others may be derived, e.g., recycle ratio, or reactant or feedstock feedrate expressed as weight hourly space velocity (WHSV) based on catalyst.

The conversion of methanol or methanol equivalents to gasoline is accomplished in contact with zeolite catalysts, such as ZSM-5, usually quantitatively in the presence of active catalyst and, in the process of the present invention, in a fixed catalyst bed. In addition to gasoline and other hydrocarbons, water is a reaction by-product. However, process variables must be carefully managed because the conversion of methanol to gasoline boiling components is a highly exothermic reaction releasing approximately 750 BTU of heat per pound of methanol. This amount of heat release will result in an adiabatic temperature increase of about 1200 degrees F. for pure methanol feed. In an adiabatic catalyst bed reactor, this large temperature increase will result in high catalyst aging rates, and possibly cause thermal damage to the catalyst. Furthermore, such high temperatures could cause an undesirable product distribution to be obtained. Therefore, it is critical to the conversion of methanol to useful products to provide sufficient heat removing or dissipating facilities particularly during initial contact with the crystalline zeolite conversion catalyst so that the maximum temperature encountered in any portion of the zeolite catalyst conversion step is below an upper predetermined limit.

The exothermic character of the conversion reaction also requires careful management of the methanol feedrate in terms of weight hourly space velocity (WHSV) based on catalyst loading. "Methanol breakthrough," a term of art indicating the appearance of methanol in the aqueous product stream and, therefore, less than quantitative conversion, has generally been followed to signal the end of the process cycle and the need to regenerate catalyst. The production of even very dilute aqueous methanol product streams presents an operator with very costly waste disposal or separation problems and must be avoided. Accordingly, when any combination of process parameters produce a methanol cycle under those conditions is ended largely for economic reasons. Of course, if disposal or recovery of unconverted methanol is not a consideration, the cycle can be continued to less than 99% methanol conversion.

Referring now to FIG. 1 a typical process flow diagram of the MTG process is presented. Crude methanol in a liquid phase condition is charged to the process by conduit 2 communicating with pump 4. The methanol is pressured to about 1500–5000 kPA, preferably 2500 kPa (350 psig), in pump 4 and then passed by conduit 6 to heat exchanger 8 wherein the liquid methanol is preheated. It is then passed into drum 9 where it is vaporized at about 185° C. (400° F.) by indirect heat exchanger 11. The methanol is then superheated in indirect exchanger 13° to about 315° C. (600° F.) and it is passed by conduit 10 to the inlet of the dimethyl ether forming catalytic reactor 12. In catalyst contained in reactor 12, a fixed bed of gamma alumina catalyst is maintained as a fixed bed of catalyst through which the methanol reactant passed downwardly through or as an annular bed of catalyst for radial flow of reactant material therethrough. A single down-flow fixed catalyst bed or a plurality of separate fixed downflow catalyst beds are arranged for converting the methanol feed under restricted temperature conditions as herein described to essentially an equilibrium product comprising methanol, dimethyl ether or water at a temperature of about 395°–415 ° C. (740°–780° F.) due to the exothermic temperature rise catalytically generated in the operation. The equilibrium product thus obtained may be construed as an ether rich product which is then passed by conduit 14 to a second reactor stage 16 housing one or more separate and sequentially arranged beds of a ZSM-5 type of crystalline zeolite.

A diluent material introduced by conduit 18 is combined with the ether rich effluent obtained as hereinbefore discussed before contact of the mixture is made with the HZSM-5 crystalline zeolite catalyst under heat generating or exothermic reaction conditions controlled to restrict the temperature increase between the reactor inlet and reactor outlet not to exceed about 94° C. (200° F.) and preferably not to exceed about 65° C. (150° F.). The conversion of the ether rich effluent by the HZSM-5 catalyst is highly exothermic as discussed above and controlled within desired limits by use of gasiform heat dissipating diluent material. During this highly exothermic operation the ether rich effluent or equilibrium mixture comprising dimethyl ether, methanol and water is controlled to effect the conversion thereof to gasoline boiling range components comprising aromatic and isoparaffins. The aromatic components comprising benzene, toluene and xylene are preferred components over the higher boiling durene aromatic material and efforts are made (e.g., reactant partial pressure, space velocity and reactant plug flow operation) to promote this end.

The product effluent of the HZSM-5 reaction zone 16 is passed through one or more cooling steps to reduce the temperature to a desired low temperature. In the specific arrangement of the figure the effluent is passed by conduit 20 to heat exchanger 22 wherein the effluent temperature is reduced to about 94° C. (200° F.) by indirect heat exchange with diluent material removed therefrom by conduit 18. The diluent will be at a temperature of about 315°–343° C. (600°–650° F.). The partially cooled effluent is removed from heat exchanger 22 and passed by conduit 24 to cooling water and/or air heat exchanger 26 wherein a further cooling of the effluent to about 38° C. (100° F.) is accomplished. Some of the effluent is passed via conduit 21 to heat exchangers 13, 11, and 8 to superheat, vaporize, and preheat, respectively, the methanol feed. The effluent from exchanger 8 is cooled in exchanger 26 and combined with cooled effluent from reactor conduit 20 and passed into separator 28, where liquid hydrocarbon, liquid water and gaseous material are separated. In the arrangement of the drawing, most of the gaseous effluent is then passed by conduit 30 to heat exchanger 22 where it is again passed in indirect heat exchange with reactor effluent and finally heater 38 before entering reactor 16. Water product is removed from separator 28 via conduit 34 for further treatment. Liquid hydrocarbon product is removed from separator 28 via conduit 32 and is sent to a product recovery section (not shown). Of course many other heat exchange arrangements may be provided for reducing the reactor effluent temperature from about 426° C. (800° F.) to about 38° C. (100 degrees F.) before passage to separator 28. Separator 28 is maintained at a temperature of about 38° C. (100° F.) and a pressure of about 1540 kPa (220 psig). In the separator a rough cut is made between gasiform diluent materials, desired aromatic and isoparaffin product and water. Water is withdrawn by conduit 34. A gasiform product material lower boiling than desired gasoline boiling range constituents is withdrawn by conduit 30 and passed to a compressor 36. A plurality of parallel arranged gas compressors may be used for this purpose. The gasiform material is compressed by compressor 36 to a pressure of about 2310 kPa (330 psig) before passage to exchanger 22. Excess gas is removed via conduit 39 and sent to product recovery.

The conversion of methanol or methanol equivalents is preferably catalyzed by a crystalline zeolite catalyst having acidic functionality. The preferred class of catalysts is characterized by a Constraint Index of 1 to 12 and a silica:alumina ratio of at least 12:1 and preferably higher e.g. 20:1 to 200:1 or even higher. As described in U.S. Pat. No. 3,998,889, the Constraint Index of a zeolite is a convenient measure of the extent to which a zeolite provides constrained access to its internal structure for molecules of different sizes. It is therefore a characteristic of the structure of the zeolite but is measured by a test which relies upon the possession of cracking activity by the zeolite. The sample of zeolite selected for determination of the Constraint Index of a zeolite should therefore represent the structure of the zeolite (manifested by its X-ray diffraction pattern) and have adequate cracking activity for the Index to be determined. If the cracking activity of the selected zeolite is too low, the Constraint Index may be determined by using a zeolite sample of the same structure but higher cracking activity which may be obtained, for example, by using an aluminosilicate zeolite of higher aluminum content. Details of the method of determining Constraint Index and of the values of the Index for typical zeolites are given in U.S. Pat. No. 3,998,899 to which reference is made for such details and other information in this respect.

The silica-alumina ratios referred to in this specification are the structural or framework ratios, that is, the ratio for the $SiO_4$ to the $AlO_4$ tetrahedra which together constitute the structure of which the zeolite is composed. This ratio may vary from the silica:alumina ratio determined by various physical and chemical methods. For example, a gross chemical analysis may include aluminum which is present in the form of cations associated with the acidic sites on the zeolite, thereby giving a low silica:alumina ratio. Similarly, if the ratio is determined by thermogravimetric analysis (TGA) of ammonia desorption, a low ammonia titration may be obtained if cationic aluminum prevents exchange of the ammonium ions onto the acidic sites. These disparities are particularly troublesome when certain treatments such as dealuminization methods which result in the presence of ionic aluminum free of the zeolite structure are employed to make highly siliceous zeolites. Due care should therefore be taken to ensure that the framework silica: alumina ratio is correctly determined.

Preferred zeolites which have the specified values of Constraint Index and silica:alumina ratio include zeolites ZSM-5, ZSM-11, ZSM-12, ZSM-35, and ZSM-48, which are described in U.S. Pat. Nos. 3,702,886 (ZSM-5), 3,709,979 (ZSM-11), 3,832,449 (ZSM-12), 4,076,842 (ZSM-23) and 4,016,245 (ZSM-35), and European Patent Publication No. 15132, and reference is made to these patents for details of these zeolites, their preparation and properties. Of these zeolites, ZSM-5 is preferred.

The zeolite catalyst used is at least partly in the hydrogen form e.g. HZSM-5 but other cations e.g. rare earth cations may also be present. When the zeolites are prepared in the presence of organic cations they may be quite inactive possibly because the intracrystalline free space is occupied by the organic cations from the forming solution. The zeolite may be activated by heating in an inert atmosphere to remove the organic cations e.g. by heating at over 500 degrees C. for 1 hour or more. The hydrogen form can then be obtained by base exchange with ammonium salts followed by calcination e.g. at 500 degrees C. in air. Other cations e.g. metal cations can be introduced by conventional base exchange techniques.

In the conventional MTG process as practiced in the art heretofore, cycle average gasoline yields generally run about 80 to 85%. Typical cycle lengths are between 20 to 40 days before methanol breakthrough at 99.9% conversion occurs. Of course, virtually every process parameter can effect yield and cycle life, at least negatively, but by and large, catalyst deactivation has a dominating effect on these properties of the process. During normal operation of the MTG reactors the zeolite catalyst undergoes gradual aging and deactivation, associated with the deposition of coke and carbonaceous materials on the catalyst. In the fixed bed system catalyst deactivation by coke causes a movement of the reaction zone toward the reactor outlet, an effect normally referred to as "band aging". This movement can be tracked by recording the catalyst bed position at which one-half the temperature rise has occurred, i.e., the temperature profile midpoint. A decrease in the value of the temperature profile midpoint is indicative of an improvement of catalyst activity during a cycle. Reactivation of catalyst will result in movement of the reactor temperature profile midpoint toward the reactor inlet.

Spent or deactivated catalyst is reactivated by swinging the reactor from process to regeneration mode by terminating the flow of feedstock to the fixed bed reactor and regenerating the catalyst by contacting it with air or other oxygen-containing gas at high temperature. As an alternate method of reactivation, it is known that a recycle gas flow, i.e., $C_4$- hydrocarbon and hydrogen , can be passed in contact with deactivated catalyst at operating conditions (2100 kPa and 350° C.) for about 24 hours. Under these conditions, catalyst activity, as measured by reactor temperature midpoint, recovers from 60% midpoint position, or closer to reactor outlet, to a 45% midpoint position, or close to reactor inlet, after deactivation and reactivation in a commercial plant operation. The interrupted flow of feedstock to the reactor is reinitiated after reactivation. Accordingly, the multiple fixed bed reactors in the process alternates between catalyst regeneration and process conversion conditions.

When used herein in relation to a zeolite which has undergone aging in an oxygenate conversion process, the term 'reactivate' is intended to mean that, after reactivation, there is an increase in the rate at which the zeolite converts oxygenates to gasoline boiling-range hydrocarbons.

The aforementioned methods of catalyst reactivation in the MTG process have distinct disadvantages. Oxidative regeneration of spent catalyst can result in catalyst damage due to the high temperatures and water formation in the combustion process. While regeneration with a recycle gas at operating conditions obviates some of the problems associated with oxidative regeneration, the extent of coke removal is less.

The new and improved reactivation technique of the present invention results in a greater activity recovery by conducting reactivation at low pressure, i.e., atmospheric pressure, with an inert gas purge rather than at elevated pressure with a recycle hydrocarbon gas purge. An improvement in regeneration under the high temperature and low pressure regeneration conditions of the present invention represents an unexpected discovery.

The following Examples 1 and 2 are provided to illustrate the present invention compared to standard reactivation procedures illustrated in Example 3.

EXAMPLE 1

An MTG process reactor, operating under typical conversion conditions of 680° F. and 2100 KPa is shut down and the flow of methanol to the process interrupted. The catalyst is allowed to cool slowly over six to ten hours while the pressure is at atmospheric under a flow of nitrogen purge gas. The reactor is brought back on stream by initiating flow of methanol to the reactor under the aforementioned conversion conditions. When finally brought back on stream the midpoint of the temperature profile position had changed from 33% before shut down to 18%. This indicates that under the flow of inert gas at reduced pressure catalyst had been reactivated to move the midpoint of the temperature profile closer to the reactor inlet. At the end of the cycle the procedure was repeated, shown in Example 2, and the reactivation occurred again with the midpoint position changing from 42% to 28%. Methanol conversion also responded favorably to the reactivations by increasing.

The following Table 1 presents the conditions and results for Examples 1, 2 and 3 of the present invention for catalyst reactivation and compares them with the conditions in Example 3.

TABLE 1

| Example | 1 | 2 | 3 |
|---|---|---|---|
| Midpoint, % | | | |
| Before React. | 33 | 42 | 63 |
| After React. | 18 | 28 | 53 |
| Relative % change | 45 | 33 | 16 |
| Methanol Conversion | | | |
| Before, wt % | 99.98 | 99.78 | 99.86 |
| After, | 99.99 | 99.89 | 99.94 |
| Change, | +0.01 | +0.11 | +0.08 |
| Methanol in Water Product | | | |
| Before, ppm wt. | 210 | 2790 | 1840 |
| After, | 160 | 1400 | 800 |
| Days on stream at Reactivation | 26 | 42 | 52 |

TABLE 1-continued

| Example | 1 | 2 | 3 |
|---|---|---|---|
| Reactivation | | | |
| Temp., °F. | 680 to 80 | 680 | 660 |
| Press., PSIG | 0 | 0 | 300 |
| Gas Type | N2 | hydrocarbon | |
| Duration, hrs | 10 | 16 | 24 |

Figure 2:
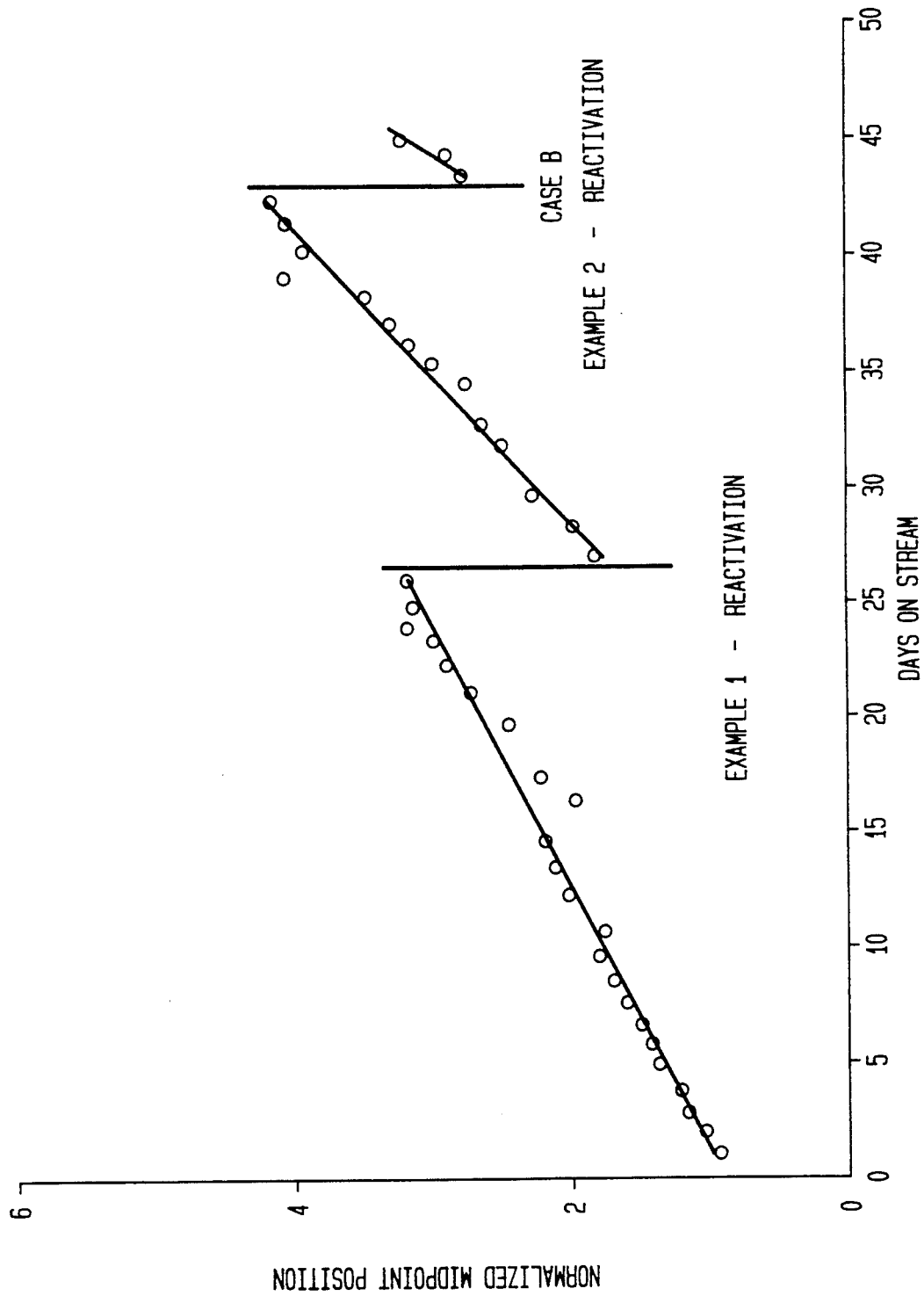
FIG. 2 is a plot of reactor midpoint temperature positions showing the recovery of activity for Examples 1 and 2 of the instant invention.
Figure 3:
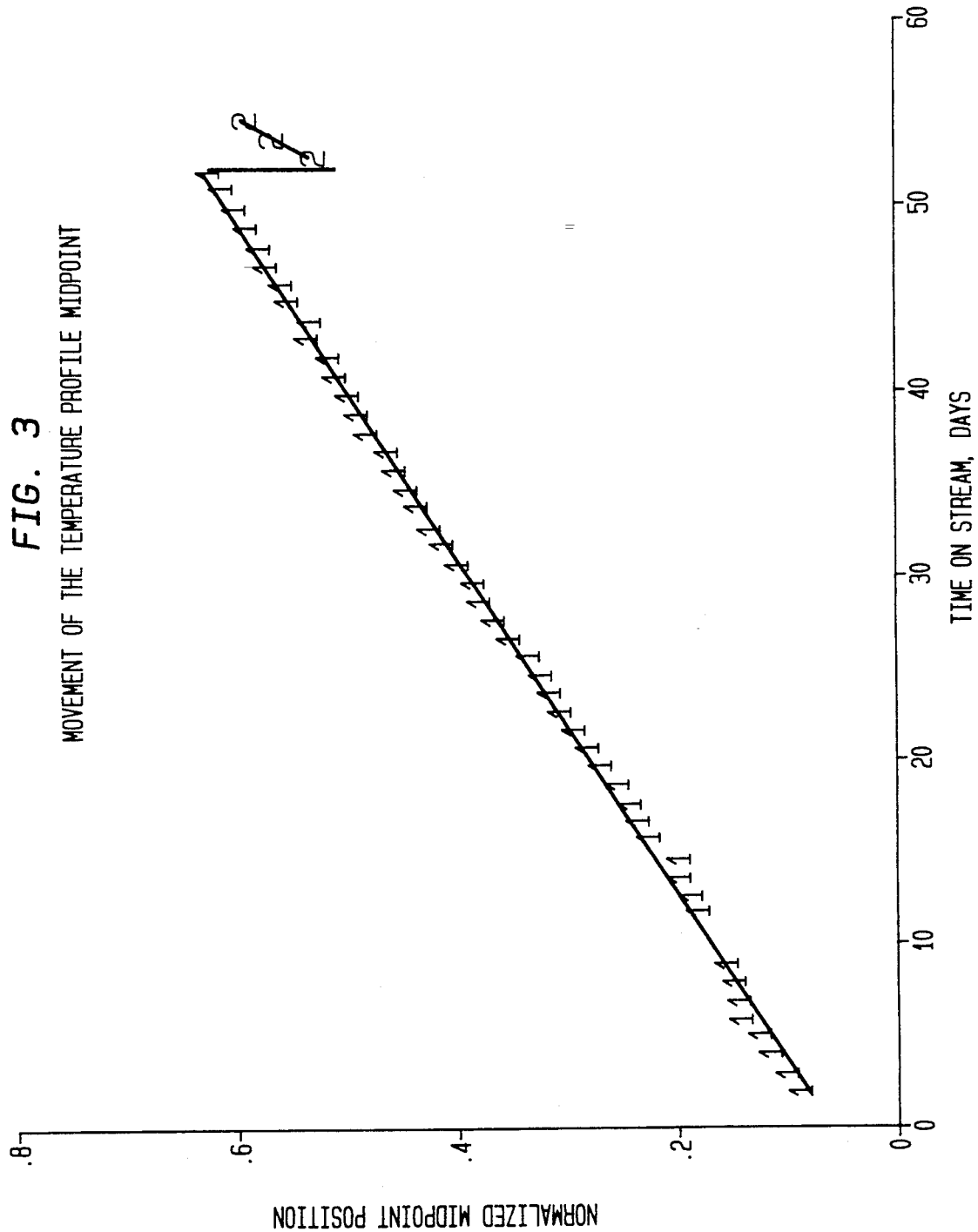
FIG. 3 is a plot of reactor midpoint temperature position for the standard reactivation procedure.
Figure 4:
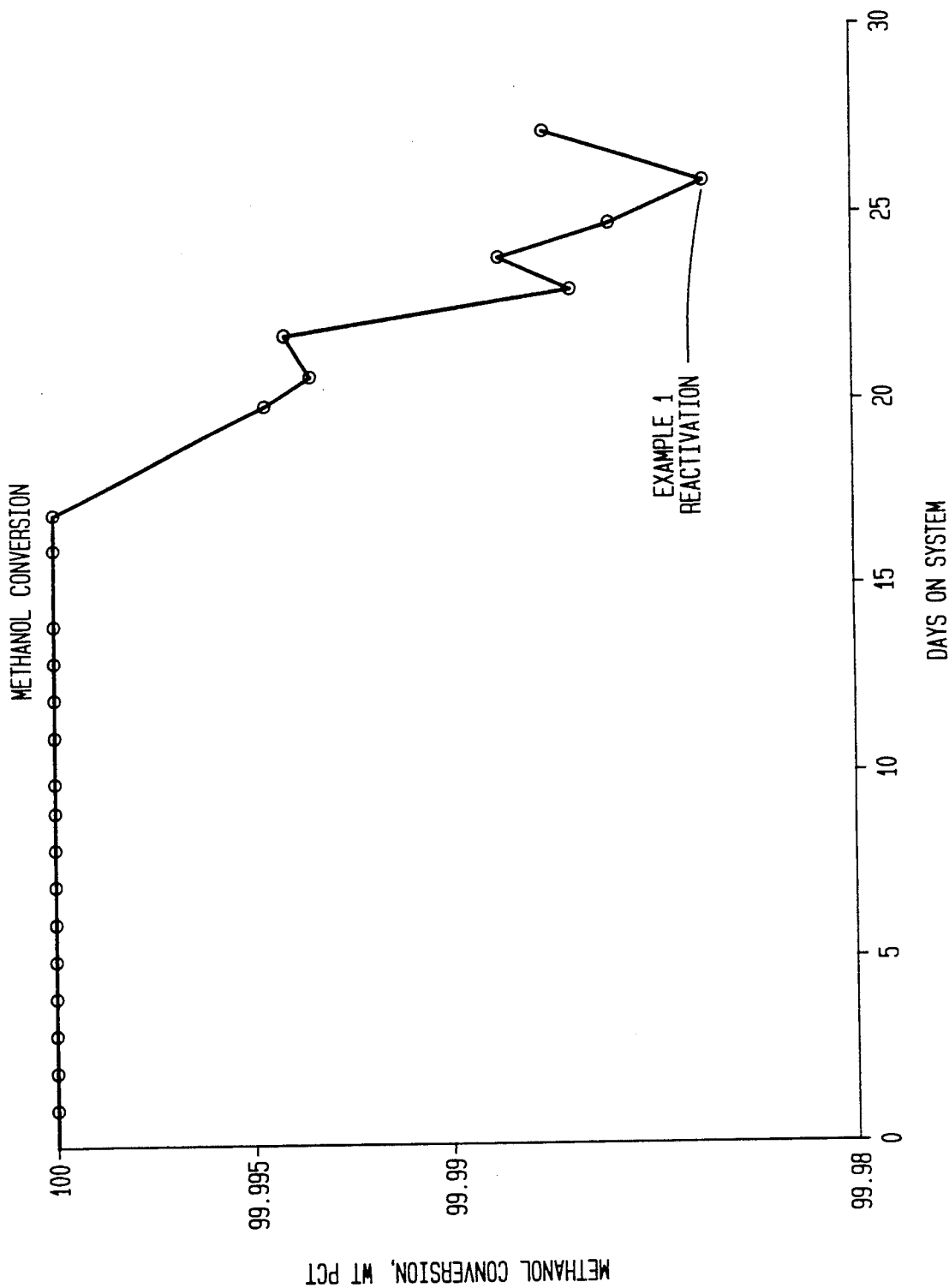
FIG. 4 is a plot of methanol conversion history for Example 1 of the invention.

The results from Examples 1, 2 and 3 are presented graphically in FIGS. 2, 3, 4, and 5. Reactor temperature midpoint positions, showing the recovery of activity, are plotted in FIG. 2 for Examples 1 and 2. The case for the standard reactivation procedure, Example 3, is plotted in FIG. 3. FIGS. 4 and 5 show the methanol conversion increase after reactivation for Examples 1 and 2 that illustrate the process of the present invention.

Comparison of FIG. 3 with FIG. 2 clearly shows that the process of the present invention as plotted for Examples 1 and 2 in FIG. 2 results in a substantially greater change in temperature profile midpoint of approximately 45% and 33%, where the case for Example 3 shows a midpoint position change of approximately 16%. Referring to Table 1, the new activation procedure is shown to result in an increase methanol conversion for Example 1, +0.11% for Example 2, and 0.08 for Example 3.

The reactivation process of this invention can be carried out using an inert gas purge comprising nitrogen, paraffinic hydrocarbons, refinery fuel gas, carbon dioxide, or gases of Group VIII of the Periodic Table of the Elements. Nitrogen (N2) is the preferred inert purge gas. The process can be carried out at pressures from subatmospheric to about 400 KPa, but operation at atmospheric pressure is preferred. Reactivation can be accomplished at conventional operating temperatures between 200°–400° C. Preferably, reactivation is initiated at approximately regular operating temperature of 360° C. The reactivation is carried out over a period of from 4–40 hours, but preferably between about 10 and 16 hours.

This new reactivation technique increases the magnitude of the benefits derived from the standard reactivation technique by moving the reactive catalyst zone (temperature midpoint) closer to the inlet of the reactor and increasing methanol conversion. This new method may allow for multiple reactivations before an oxygen regeneration is needed. This possibility is enhanced, for example, by the availability of vacuum facilities in many commercial regeneration systems. This will result in reduced operating costs and increased catalyst life which will reduce catalyst costs. Since no thermal shocking of the catalyst is involved because temperature is kept constant (unlike during oxygen regenerations) catalyst breakage should be reduced.

While the instant invention has been described by specific examples and embodiments, there is no intent to limit the inventive concept except as set forth in the following claims.

What is claimed is:

1. In a fixed bed process for the conversion of $C_1$–$C_4$ oxygenates in contact with acidic, medium pore, shape selective zeolite catalyst particles to produce gasoline boiling range hydrocarbons, including the step of reactivating spent catalyst at super atmospheric process pressure and elevated temperature, the improvement comprising:

reactivating said spent catalyst at pressure less than about 1400 kPa and temperature between about 300° C. and 400° C. in contact with a stream of inert purge gas for a time period of from about 4 hours to about 40 hours.

2. The process of claim 1 wherein said improvement comprises a reactivating pressure of about atmospheric pressure.

3. The process of claim 1 wherein said inert purge gas includes $N_2$, light paraffinic hydrocarbons, refinery fuel gas and Group VIII gases of the Periodic Table of the Elements.

4. The process of claim 1 where in the improvement comprises reactivating said spent catalyst using predominantly nitrogen purge gas.

5. The process of claim 1 wherein the improvement comprises reactivating said spent catalyst at a temperature of about 360° C.

6. The process of claim 1 wherein said catalyst comprises aluminosilicate having a constraint index of 1–12 and a silica/alumina molar ratio of at least 12.

7. The process of claim 1 wherein said catalyst comprises ZSM-5.

8. A process for the conversion of lower aliphatic oxygenated hydrocarbon to gasoline or gasoline and distillate boiling range hydrocarbons, comprising;
 a) passing said feedstock through a reactor containing a fixed bed of acidic shape selective medium pore zeolite catalyst particles at conditions sufficient to effect said conversion;
 b) separating effluent from said reactor and recovering said gasoline or gasoline and distillate boiling range hydrocarbons;
 c) interrupting feedstock flow to said reactor upon catalyst deactivation and loss in feedstock conversion rate;
 d) passing inert purge gas to said reactor at temperature between about 300° C. and 400° C. and pressure less than about 1400 kPa for a time period of from about 4 hours to about 40 hours whereby deactivated catalyst in said reactor is reactivated.

9. The process of claim 8 wherein said inert purge gas is passed to said reactor at about atmospheric pressure.

10. The process of claim 8 wherein said inert purge gas includes $N_2$, light paraffinic hydrocarbons and Group VIII gases of the IUPAC Periodic Table of the Elements.

11. The process of claim 8 wherein said spent catalyst is reactivated using nitrogen as purge gas.

12. The process of claim 8 wherein said spent catalyst is reactivated at a temperature of about 360° C.

13. The process of claim 8 wherein said catalyst comprises aluminosilicate having a constraint index of 1–12 and a silica/alumina molar ratio of at least 12.

14. The process of claim 8 wherein said catalyst comprises ZSM-5.

15. The process of claim 8 wherein said feedstock comprises methanol, dimethylether or mixtures thereof and said hydrocarbons comprise $C_5+$ gasoline boiling range hydrocarbons.

16. A process for the reactivation of fixed bed of spent acidic, medium pore, shape selective zeolite catalyst particles employed in a process for the catalytic conversion of $C_1$–$C_4$ oxygenates feedstream to gasoline boiling range hydrocarbons, comprising:

contacting said spent catalyst with a stream of inert purge gas in the absence of said oxygenates feedstream and at a temperature between 200° C. and 400° C. and pressure less than 1400 kPa for a time period of from about 4 hours to about 40 hours, sufficient to reactivate said spent catalyst.

17. The process of claim 16 wherein said reduced pressure is about atmospheric pressure.

18. The process of claim 16 wherein said inert purge gas includes $N_2$, light paraffinic hydrocarbons, refinery fuel gas and Group VIII gases of the Periodic Table of the Elements.

19. The process of claim 16 wherein said spent catalyst is reactivated using nitrogen as purge gas.

20. The process of claim 16 wherein said spent catalyst is reactivated at a temperature of about 360° C.

* * * * *